US012629350B2

(12) United States Patent
Sawashita et al.

(10) Patent No.: US 12,629,350 B2
(45) Date of Patent: May 19, 2026

(54) TRANSTHYRETIN TETRAMER STABILIZING AGENT, AND PREVENTING AGENT OR PROGRESSION SUPPRESSING AGENT FOR TRANSTHYRETIN AMYLOIDOSIS

(71) Applicants: KANEKA CORPORATION, Osaka (JP); EDUCATIONAL FOUNDATION KYUSHU BUNKA GAKUEN, Sasebo (JP); NATIONAL UNIVERSITY CORPORATION KUMAMOTO UNIVERSITY, Kumamoto (JP)

(72) Inventors: Jinko Sawashita, Osaka (JP); Yukio Ando, Sasebo (JP); Hiroaki Matsushita, Sasebo (JP); Mitsuharu Ueda, Kumamoto (JP); Teruaki Masuda, Kumamoto (JP); Yohei Misumi, Kumamoto (JP)

(73) Assignees: KANEKA CORPORATION, Osaka (JP); EDUCATIONAL FOUNDATION KYUSHU BUNKA GAKUEN, Sasebo (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 451 days.

(21) Appl. No.: 18/131,695

(22) Filed: Apr. 6, 2023

(65) Prior Publication Data

US 2023/0241022 A1      Aug. 3, 2023

Related U.S. Application Data

(63) Continuation of application No. PCT/JP2021/037040, filed on Oct. 6, 2021.

(30) Foreign Application Priority Data

Oct. 7, 2020    (JP) .................................. 2020-169842

(51) Int. Cl.
*A61K 31/353*        (2006.01)
*A61P 1/00*          (2006.01)

(52) U.S. Cl.
CPC .............. *A61K 31/353* (2013.01); *A61P 1/00* (2018.01)

(58) Field of Classification Search
CPC ........ A61K 31/352; A61K 31/353; A61P 1/00
(Continued)

(56) References Cited

U.S. PATENT DOCUMENTS

2007/0098761 A1    5/2007   Arai et al.
2009/0041876 A1    2/2009   Kitano et al.

FOREIGN PATENT DOCUMENTS

CN        103989907 A      8/2014
CN        104587161 A      5/2015
(Continued)

OTHER PUBLICATIONS

EFSA Panel on Dietetic Products, Nutrition and Allergies (NDA), "Scientific Opinion on the safety of 'Glavonoid', an extract derived from the roots or rootstock of *Glycyrrhiza glabra* L., as a Novel Food ingredient," EFSA Journal, vol. 9, No. 7, 2011, pp. 1-27.
(Continued)

*Primary Examiner* — Taylor V Oh
(74) *Attorney, Agent, or Firm* — Birch, Stewart, Kolasch & Birch, LLP

(57) ABSTRACT

Provided are a transthyretin tetramer stabilizing agent and a preventing agent or progression suppressing agent for transthyretin amyloidosis. The present invention relates to a transthyretin tetramer stabilizing agent including glabridin,
(Continued)

t-test mean±SD (n=3)

O: Added with glabridin
●: Added with medium-chain fatty acid triglyceride solution containing polyphenol mixture
(The unit denotes the concentration of glabridin added.)

glabrene, and glabrol, and to a preventing agent or progression suppressing agent for transthyretin amyloidosis including glabridin, glabrene, and glabrol.

15 Claims, 2 Drawing Sheets

(58) Field of Classification Search
USPC .......................................................... 514/454
See application file for complete search history.

(56) References Cited

FOREIGN PATENT DOCUMENTS

| JP | 2007-63161 A | 3/2007 |
|----|--------------|--------|
| JP | 2017-96785 A | 6/2017 |
| JP | 2020-7236 A | 1/2020 |

OTHER PUBLICATIONS

Extended European Search Report for European Application No. 21877675.5, dated Oct. 9, 2024.

Arif et al., "In Silico Inhibition of BACE-1 by Selective Phytochemicals as Novel Potential Inhibitors: Molecular Docking and DFT Studies", Current Drug Discovery Technologies, Jun. 2020, vol. 17, Issue 3, pp. 397-411.

International Search Report for PCT/JP2021/037040 (PCT/ISA/210) mailed on Dec. 21, 2021.

Matsushita et al., "Glavonoid, a possible supplement for prevention of ATTR amyloidosis", Heliyon, Oct. 5, 2021, vol. 7, Issue 10, e08101, total 7 pages.

Written Opinion of the International Searching Authority for PCT/JP2021/037040 (PCT/ISA/237) mailed on Dec. 21, 2021.

Yokoyama et al., "Crystal Structures of Human Transthyretin Complexed with Glabridin", Journal of Medicinal Chemistry, 2014, vol. 57, Issue 3, pp. 1090-1096.

Yokoyama et al., "Inhibition of the Amyloidogenesis of Transthyretin by Natural Products and Synthetic Compounds", Biol. Pharm. Bull., 2018, vol. 41, No. 7, pp. 979-984.

t-test  mean±SD (n=3)

TRANSTHYRETIN TETRAMER STABILIZING AGENT, AND PREVENTING AGENT OR PROGRESSION SUPPRESSING AGENT FOR TRANSTHYRETIN AMYLOIDOSIS

CROSS-REFERENCE TO RELATED APPLICATIONS

This application is a Continuation of PCT International Application No. PCT/JP2021/037040, filed on Oct. 6, 2021, which claims priority under 35 U.S.C. § 119(a) to Patent Application No. 2020-169842, filed in Japan on Oct. 7, 2020, all of which are hereby expressly incorporated by reference into the present application.

TECHNICAL FIELD

The present invention relates first to a transthyretin tetramer stabilizing agent for stabilizing transthyretin tetramer.

The present invention relates secondly to a transthyretin amyloidosis preventing agent or progression suppressing agent for treating, preventing, or suppressing the progression of, transthyretin amyloidosis in which amyloid fibrils formed by the abnormal aggregation of transthyretin are deposited.

BACKGROUND ART

Transthyretin is a β-sheet-rich homotetramer protein in which one subunit is constituted by 127 amino acid residues. It is known that transthyretin has a function by which to bind to and transport thyroxine (T4) in the blood and the cerebrospinal fluid. A transthyretin tetramer has two thyroxine binding sites (T4 binding sites) in the dimer-dimer link (Non-Patent Literature 1).

Transthyretin tetramer is usually stable under physiological conditions, but is destabilized by factors, such as aging or genetic abnormality, and thus dissociated into monomers, which in turn undergo misfolding to thereby become aggregates of amyloidogenic intermediates, with the result that the aggregates are formed into amyloids, thus causing the deposition of amyloid fibrils and inducing clinical symptoms of amyloidosis. Examples of known transthyretin amyloidoses include: familial amyloid polyneuropathy (FAP) in which genetically variant transthyretins (for example, V30M variant transthyretins) are formed into amyloids, which are deposited in various organs in the whole body, thus inducing organopathy; senile systemic amyloidosis (SSA) in which wild-type transthyretins are formed into amyloids through aging, and deposited in the heart, tendon, and the like, inducing a disease; and the like.

The stabilization of a transthyretin tetramer and suppression of amyloid formation can be achieved with a low-molecular-weight compound that binds to a T4 binding site of transthyretin. Such a compound has led to the development of various pharmaceutical products, which, however, cause a side effect, and besides, involve a high cost for one dose, hence imposing a large burden on a patient. In addition, transthyretin amyloidosis is a disease that is not only difficult to cure completely, once developed, but also develops with a high probability along with aging, and accordingly, is attracting attention to develop preventive measures.

Non-Patent Literature 1 and Non-Patent Literature 2 state that two molecules of glabridin, which is one of licorice glabra polyphenols, have the effect of binding to and stabilizing a transthyretin tetramer, thus suppressing the formation of amyloid fibrils.

Licorice is a plant belonging to Fabaceae *Glycyrrhiza* and widely distributed in China, Europe, Russia, Afghanistan, Iran, Pakistan, and the like, and is a plant having a long history of ingestion in which the root and the like of the plant have been utilized as food and herbal medicine.

CITATION LIST

Non-Patent Literature

Non-Patent Literature 1: Yokoyama, T. et al., *Biol. Pharm. Bull.* 41, 979-984 (2018)
Non-Patent Literature 2: Yokoyama, T. et al., *J. Med. Chem.* 57, 1090-1096 (2014)

SUMMARY OF INVENTION

Technical Problem

The present invention is directed to preventing, treating or suppressing the progression of, transthyretin amyloidosis, for which the stabilization of a transthyretin tetramer is effective. Hence, the invention makes it possible to develop a stabilizing preparation for a transthyretin tetramer, and to administer the preparation to a patient before disease onset thus making it possible to prevent transthyretin amyloidosis. In view of this, an object of the present invention is to provide a transthyretin tetramer stabilizing agent, and a preventing agent or progression suppressing agent for transthyretin amyloidosis.

Solution to Problem

As above-mentioned, Non-Patent Literature 1 and Non-Patent Literature 2 describe glabridin as singularly contributing to the stabilization of a transthyretin tetramer, but no study has conventionally been made on the effect that a mixture containing glabridin and besides another polyphenol compound has for the stabilization of a transthyretin tetramer.

The present inventors have made intensive studies, and as a result, have come to complete the following invention through the discovery that a polyphenol mixture containing glabridin, glabrene, and glabrol is effective particularly as an active component of a transthyretin tetramer stabilizing agent and an active component of a preventing agent, treatment agent or progression suppressing agent for transthyretin amyloidosis.

Thus, the present invention is directed to:

(1) A transthyretin tetramer stabilizing agent including glabridin, glabrene, and glabrol.
(2) The agent according to (1), further including 4'-O-methylglabridin.
(3) The agent according to (2), wherein the agent exhibits any one or more of the characteristics b), c), and d) under the following conditions a) in an HPLC analysis:
a) mobile phase: acetonitrile:methanol=1:1 (mobile phase A) and 20 mM phosphoric acid (mobile phase B) in gradient elution; column: ODS column; flow rate: 1.0 mL/minute; temperature: 40° C.; detector: UV detector; and wavelength of detection: 282 nm;
b) a ratio of a glabrene peak intensity to a glabridin peak intensity is 38% or more and 41% or less;

c) a ratio of a glabrol peak intensity to a glabridin peak intensity is 44% or more and 47% or less; and d) a ratio of a 4'-O-methylglabridin intensity to a glabridin peak intensity is 15% or more and 20% or less.

(4) The agent according to any one of (1) to (3), wherein the content of glycyrrhizic acid is 0.005 wt % or less.

(5) A preventing agent or progression suppressing agent for transthyretin amyloidosis including glabridin, glabrene, and glabrol.

(6) The agent according to (5), wherein the transthyretin amyloidosis is senile systemic amyloidosis or familial amyloid polyneuropathy.

(7) The agent according to (5) or (6), further including 4'-O-methylglabridin.

(8) The agent according to (7), wherein the agent exhibits any one or more of the characteristics b), c), and d) under the following conditions a) in an HPLC analysis:

a) mobile phase: acetonitrile:methanol=1:1 (mobile phase A) and 20 mM phosphoric acid (mobile phase B) in gradient elution; column: ODS column; flow rate: 1.0 mL/minute; temperature: $40°$ C.; detector: UV detector; and wavelength of detection: 282 nm;

b) a ratio of a glabrene peak intensity to a glabridin peak intensity is 38% or more and 41% or less;

c) a ratio of a glabrol peak intensity to a glabridin peak intensity is 44% or more and 47% or less; and d) a ratio of a 4'-O-methylglabridin intensity to a glabridin peak intensity is 15% or more and 20% or less.

(9) The agent according to any one of (1) to (8), in the form of a tablet, a capsule, a granule, or a powder.

(10) The agent according to any one of (1) to (9), including the glabridin in an amount of 4 mg to 1200 mg per one ingestion or dosage unit.

(12) Use of a polyphenol mixture including glabridin, glabrene, and glabrol, for the manufacture of a composition for stabilizing a transthyretin tetramer.

Here, the composition is preferably in the form of a tablet, a capsule, a granule, or a powder. In addition, the composition preferably contains glabridin in an amount of 4 mg to 1200 mg per one ingestion or dosage.

(13) Use of a polyphenol mixture including glabridin, glabrene, and glabrol, for the manufacture of a pharmaceutical for stabilizing a transthyretin tetramer.

Here, the pharmaceutical is preferably in the form of a preparation for oral administration, such as a tablet, a capsule, a granule, or a powder. In addition, the pharmaceutical preferably contains glabridin in an amount of 4 mg to 1200 mg per one ingestion or dosage unit.

(14) A method of stabilizing a transthyretin tetramer ex vivo, including:

bringing a polyphenol mixture including glabridin, glabrene, and glabrol in contact with the transthyretin tetramer present ex vivo; and suppressing the monomerization of the transthyretin tetramer and/or the formation of amyloid fibrils derived from the transthyretin tetramer.

(15) A method of stabilizing transthyretin tetramers in a subject, including:

administering a polyphenol mixture including glabridin, glabrene, and glabrol to a subject in need of the stabilization of the transthyretin tetramer; and suppressing, in the subject, the monomerization of the transthyretin tetramer and/or the formation of amyloid fibrils derived from the transthyretin tetramer.

Here, in the administration, a composition containing the polyphenol mixture and prepared in the form of a preparation for oral administration, such as a tablet, a capsule, a granule, or a powder, is preferably orally administered to the subject. In addition, in the administration, the polyphenol mixture is preferably administered in such a manner that the total amount of the polyphenol per day is 0.01 to 100 mg/kg of body weight, preferably 0.1 to 30 mg/kg of body weight.

(16) A polyphenol mixture including glabridin, glabrene, and glabrol, for stabilizing a transthyretin tetramer ex vivo or in vivo.

(17) The use according to (12), the use according to (13), the method according to (14), the method according to (15), or the polyphenol mixture according to (16), wherein the polyphenol mixture further contains 4'-O-methylglabridin.

Here, the polyphenol mixture further containing 4'-O-methylglabridin more preferably exhibits any one or more of the characteristics b), c), and d) under the following conditions a) in an HPLC analysis:

a) mobile phase: acetonitrile:methanol=1:1 (mobile phase A) and 20 mM phosphoric acid (mobile phase B) in gradient elution; column: ODS column; flow rate: 1.0 mL/minute; temperature: $40°$ C.; detector: UV detector; and wavelength of detection: 282 nm;

b) a ratio of a glabrene peak intensity to a glabridin peak intensity is 38% or more and 41% or less;

c) a ratio of a glabrol peak intensity to a glabridin peak intensity is 44% or more and 47% or less; and d) a ratio of a 4'-O-methylglabridin intensity to a glabridin peak intensity is 15% or more and 20% or less.

(18) The use according to (12), the use according to (13), the method according to (14), the method according to (15), or the polyphenol mixture according to (16), wherein the amount of glycyrrhizic acid contained in the polyphenol mixture is 0.005 wt % or less.

(19) Use of a polyphenol mixture including glabridin, glabrene, and glabrol, for the manufacture of a composition for preventing, or suppressing the progression of, transthyretin amyloidosis.

Here, the composition is preferably in the form of a tablet, a capsule, a granule, or a powder. In addition, the composition preferably contains glabridin in an amount of 4 mg to 1200 mg per one ingestion or dosage unit.

(20) Use of a polyphenol mixture including glabridin, glabrene, and glabrol, for the manufacture of a pharmaceutical for preventing, or suppressing the progression of, transthyretin amyloidosis.

Here, the pharmaceutical is preferably in the form of a preparation for oral administration, such as a tablet, a capsule, a granule, or a powder. In addition, the pharmaceutical preferably contains glabridin in an amount of 4 mg to 1200 mg per one ingestion or dosage unit.

(21) A method of preventing, or suppressing the progression of, transthyretin amyloidosis in a subject, including:

administering a polyphenol mixture including glabridin, glabrene, and glabrol to a subject in need of the prevention of, or the suppression of progression of, transthyretin amyloidosis; and suppressing, in the subject, the monomerization of a transthyretin tetramer and/or the formation of amyloid fibrils from the transthyretin tetramer.

Here, in the administration, a composition containing the polyphenol mixture and prepared in the form of a preparation for oral administration, such as a tablet, a capsule, a granule, or a powder, is preferably orally administered to the subject. In addition, in the administration, the polyphenol mixture is preferably administered in such a manner that the total amount of the polyphenol per day is 0.01 to 100 mg/kg of body weight, preferably 0.1 to 30 mg/kg of body weight.

(22) A polyphenol mixture including glabridin, glabrene, and glabrol, for preventing, or suppressing the progression of, transthyretin amyloidosis.

(23) The use according to (19), the use according to (20), the method according to (21), or the polyphenol mixture according to (22), wherein the transthyretin amyloidosis is senile systemic amyloidosis or familial amyloid polyneuropathy.

(24) The use according to (19), the use according to (20), the method according to (21), or the polyphenol mixture according to (22), wherein the polyphenol mixture further contains 4'-0-methylglabridin.

Here, the polyphenol mixture further containing 4'-O-methylglabridin more preferably exhibits any one or more of the characteristics b), c), and d) under the following conditions a) in an HPLC analysis:

a) mobile phase: acetonitrile:methanol=1:1 (mobile phase A) and 20 mM phosphoric acid (mobile phase B) in gradient elution; column: ODS column; flow rate: 1.0 mL/minute; temperature: 40° C.; detector: UV detector; and wavelength of detection: 282 nm;

b) a ratio of a glabrene peak intensity to a glabridin peak intensity is 38% or more and 41% or less;

c) a ratio of a glabrol peak intensity to a glabridin peak intensity is 44% or more and 47% or less; and d) a ratio of a 4'-O-methylglabridin intensity to a glabridin peak intensity is 15% or more and 20% or less.

(25) The use according to (19), the use according to (20), the method according to (21), or the polyphenol mixture according to (22), wherein the amount of glycyrrhizic acid in the polyphenol mixture is 0.005 wt % or less.

The present description includes the contents disclosed in Japanese Patent Application No. 2020-169842, which is a priority document of the present application.

Advantageous Effects of Invention

A transthyretin tetramer stabilizing agent according to the present invention makes it possible to maintain transthyretin tetramer stably, and makes it possible to suppress the monomerization of the tetramer and the formation of amyloid fibrils.

A preventing agent, treatment agent or progression suppressing agent for transthyretin amyloidosis according to the present invention can prevent or suppress transthyretin amyloidosis, such as familial amyloid polyneuropathy (FAP) or senile systemic amyloidosis (SSA).

DESCRIPTION OF EMBODIMENTS

<Polyphenol>

Figure 1:
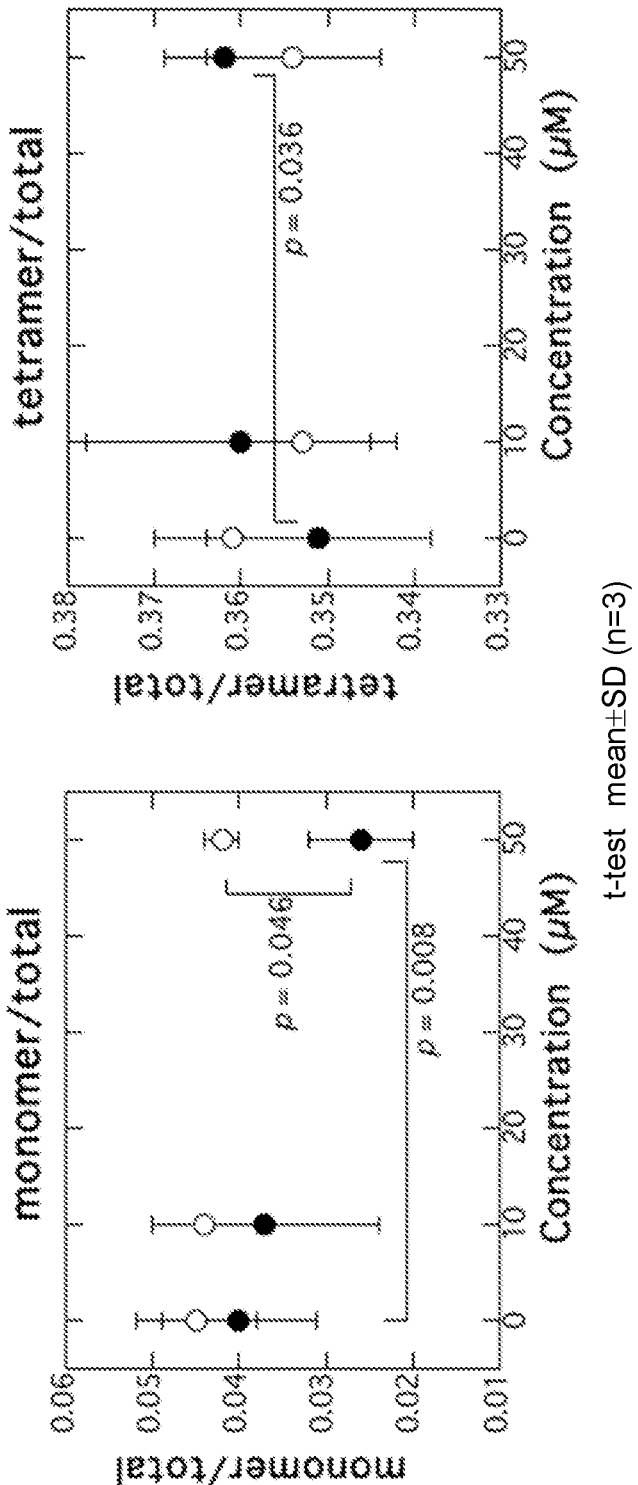
FIG. 1 The left graph in FIG. 1 illustrates the ratios of the transthyretin monomers to the total amount of the transthyretins (monomer/total) in serums in Example 3, in which the serums had been added with a medium-chain fatty acid triglyceride solution containing a polyphenol mixture and with glabridin in such a manner that the amounts of the glabridin were 0, 10, and 50 μM respectively, and the resulting serums had been incubated. The right graph in FIG. 1 shows the ratios of the transthyretin tetramers to the total amount of the transthyretins (tetramer/total) in serums in Example 3, in which the serums had been added with a medium-chain fatty acid triglyceride solution containing a polyphenol mixture and with glabridin in such a manner that the amounts of the glabridin were 0, 10, and 50 μM respectively, and the resulting serums had been incubated. The white circles represent the ratios in the serums supplemented with the glabridin. The black circles represent the ratios in the serums supplemented with the medium-chain fatty acid triglyceride solution containing a polyphenol mixture.

A transthyretin tetramer stabilizing agent and a preventing agent, treatment agent or progression suppressing agent for transthyretin amyloidosis according to the present invention includes glabridin, glabrene, and glabrol as effective components, and more preferably further contains 4'-O-methylglabridin. Herein, a combination of the polyphenols to be used as effective components is referred to as a "polyphenol mixture" in some cases. The present inventors have discovered that the polyphenol mixture has a markedly higher effect of stabilizing a transthyretin tetramer, compared with use of glabridin alone, which is conventionally known for achieving the effect of stabilizing the transthyretin tetramer.

The polyphenols contained in the polyphenol mixture belongs to a group of compounds classified into prenylflavonoids, and have a structure in which one or more C5 isoprene units are bound to diphenyl propane.

The polyphenol mixture may further contain another polyphenol, such as glycycoumarin, glycyrol, glycyrin, liquiritigenin, glicoricone, 3'-hydroxy-4'-O-methylglabridin, glyurallin B, licocoumarone, gancaonin I, dehydroglyasperin D, echinatin, isolicoflavonol, dehydroglyasperin C, glyasperin B, glycyrrhisoflavanone, lupiwighteone, glyasperin D, and semilicoisoflavone B.

Additional examples of the other polyphenol include genistein, daidzein, quercetin, rutin, catechin, epigallocatechin gallate, hesperidin, nobiletin, tyrosol, hydroxy tyrosol, oleuropein, naringenin, caffeic acid, apple polyphenol, tea polyphenol, gallic acid, and the like. The other polyphenol is preferably genistein, daidzein, quercetin, rutin, catechin, epigallocatechin gallate, hesperidin, nobiletin, naringenin, caffeic acid, apple polyphenol, or tea polyphenol. These other polyphenols may be used singularly, or used in mixture of two or more kinds thereof.

Each polyphenol in the polyphenol mixture may be present in the form of a salt, an ester, a glycoside, or the like. Examples of the salt of a polyphenol include: a salt with an acid acceptable in the final applications, such as pharmaceutical products, food or drink product, and animal feeding stuff, examples of which acid include hydrochloric acid, sulfuric acid, methanesulfonic acid, fumaric acid, maleic acid, succinic acid, acetic acid, benzoic acid, oxalic acid, citric acid, tartaric acid, carbonic acid, or phosphoric acid; a salt with a base acceptable in the final applications, examples of which salt include an alkali metal salt, for example, a sodium or potassium salt; an alkaline earth metal salt, for example, a calcium or magnesium salt; and a salt with a suitable organic ligand, for example, quaternary ammonium. Examples of the ester of a polyphenol include a fatty acid ester, specific examples of which include: an ester with a long-chain fatty acid, such as oleic acid, palmitic acid, stearic acid, linoleic acid, or linolenic acid; and an ester with a short- or medium-chain fatty acid, such as acetic acid or butyric acid. Examples of a glycoside of a polyphenol include a glycoside in which a sugar component, such as a monosaccharide, a disaccharide, a trisaccharide, an oligosaccharide, or a polysaccharide is bound.

The polyphenol mixture may be contained, in the form of a hydrophobic licorice extract or a purified product thereof, in a transthyretin tetramer stabilizing agent, and preventing agent, treatment agent or progression suppressing agent for transthyretin amyloidosis according to the present invention.

Each polyphenol in the polyphenol mixture may be that which is chemically synthesized. Each polyphenol in the polyphenol mixture may be that which has been extracted from a biological sample, such as a plant, a microorganism, or an animal, and, if desired, purified. Each polyphenol in the polyphenol mixture may be produced by fermentation using a microorganism having the capability to produce the polyphenol. The microorganism having the capability to produce the polyphenol may be a genetically engineered microorganism, or may be a wild-type microorganism.

In a preferable embodiment, the polyphenol mixture is preferably mixed so as to exhibit any one or more, more preferably two or more, particularly preferably all, of the characteristics b), c), and d) under the following conditions a) in an HPLC analysis:

a) mobile phase: acetonitrile:methanol=1:1 (mobile phase A) and 20 mM phosphoric acid (mobile phase B) in gradient elution; column: ODS column; flow rate: 1.0 mL/minute; temperature: 40° C.; detector: UV detector; and wavelength of detection: 282 nm;

b) a ratio of a glabrene peak intensity (peak area) to a glabridin peak intensity (peak area) is 38% or more and 41% or less;

c) a ratio of a glabrol peak intensity (peak area) to a glabridin peak intensity (peak area) is 44% or more and 47% or less; and d) a ratio of a 4'-O-methylglabridin intensity (peak area) to a glabridin peak intensity (peak area) is 15% or more and 20% or less.

The ratio of a glabrene peak intensity (peak area) to a glabridin peak intensity (peak area) is subject to no particular limitation as long as the ratio is within the range. The lower limit of the peak intensity is, for example, preferably 38% or 39%, and the upper limit is preferably 41% or 40%.

The ratio of a glabrol peak intensity (peak area) to a glabridin peak intensity (peak area) is subject to no particular limitation as long as the ratio is within the range. The lower limit of the peak intensity is, for example, preferably 44% or 45%, and the upper limit is preferably 47%, or 46%.

The ratio of a 4'-O-methylglabridin peak intensity (peak area) to a glabridin intensity (peak area) is subject to no particular limitation as long as the ratio is within the range. The lower limit of the peak intensity is, for example, preferably 15%, 16%, or 17%, and the upper limit is preferably 20%, 19%, or 18%.

In the above-mentioned a), the gradient of the mobile phase A and the mobile phase B is a condition in which the ratio of the mobile phase A to the total amount of the mobile phase A and the mobile phase B is preferably constant at 50% (v/v) after the start of analysis until 20 minutes after the start, then increased to 80% (v/v) at a constant ratio after the 20 minutes until 75 minutes, then constant at 100% (v/v) after the 75 minutes until 80 minutes, and constant at 50% (v/v) after the 80 minutes until 100 minutes.

In the above-mentioned a), for example, a YMC J'sphere ODS-H80 (YMC Co., Ltd.) can be used as the ODS column. The size of the ODS column is, for example, 4.6 mm in inner diameter×250 mm in length.

Examples of a method of measuring the amount of a polyphenol include: a colorimetric method, such as a ferrous tartrate method, a Prussian blue method, a Folin-Ciocalteau method, or a Folin-Denis method; and an HPLC method for component-by-component measurement. Any of the measurement methods may be used. For the measurement of the amount of the whole polyphenol, a Folin-Denis method or a Folin-Ciocalteau method is often used. With a Folin-Denis method or a Folin-Ciocalteau method, using a standard substance makes it possible to prepare a calibration curve based on the standard substance, and to make a measurement in terms of the standard substance. For example, glabridin can be used as a standard substance. Specifically, for example, using the below-mentioned method described in the Examples section, the amount of the polyphenol components contained in the transthyretin tetramer stabilizing agent, and the preventing agent or progression suppressing agent for transthyretin amyloidosis according to the present invention can be determined as a value in terms of glabridin.

<Hydrophobic Licorice Extract>

As above-mentioned, the polyphenol mixture can be used in the form of a licorice extract. In this embodiment, a licorice to be used as a raw material for an extract is subject to no particular limitation as long as the licorice is a plant belonging to *Glycyrrhiza*. Specific examples of licorices include *Glycyrrhiza uralensis* (*G. uralensis*), *Glycyrrhiza inflata* (*G. inflata*), *Glycyrrhiza glabra* (*G. glabra*), *Glycyrrhiza eurycarpa* (*G. eurycarpa*), *Glycyrrhiza aspera* (*G. aspera*), and the like. Preferable examples include *G. uralensis, G. inflata, G. glabra*, and the like. Still more preferable examples include *G. glabra*.

A part of a plant, when used to obtain a licorice extract, is subject to no particular limitation. The whole plant or any part of a licorice, such as a leaf, stem, root (rhizome), flower, seed, or the like, may be used.

Glabridin, glabrene, and glabrol are hydrophobic, and hence, a hydrophobic licorice extract can be used as a licorice extract.

The hydrophobic licorice extract containing the polyphenol mixture can be an extract obtained by extracting a hydrophobic component from a licorice. Examples of the extract include: a liquid extract containing an extraction solvent of a licorice; such a concentrate or dried material of the liquid extract as obtained by removing part or all of the extraction solvent from the liquid extract; and a treated material of the liquid extract, the concentrate, or the dried material. Examples of the treated material include a dilution of the liquid extract, the concentrate, or the dried material; and a treated material having a polyphenol concentration increased by concentrating or purifying (or partially purifying) the polyphenol in the liquid extract, the concentrate, or the dried material. A method of obtaining a hydrophobic licorice extract from a licorice is subject to no particular limitation. For example, a hydrophobic component can be obtained from a licorice or a powder thereof, cultured cells of a licorice, or the like by extraction using an organic solvent, or by the like. Alternatively, a hydrophilic component is preliminarily extracted or removed from a licorice using water or an alkaline water solution. Then, from the licorice residue or the residue dried, a hydrophobic component in the licorice can be obtained by extraction using an organic solvent. Alternatively, an extract can be obtained by using another kind of organic solvent to further extract the hydrophobic extract once extracted by the above-mentioned method.

An organic solvent to be used as an extraction solvent is preferably that which is permitted to be used for producing or processing pharmaceutical products, food products, food additives, and the like. Examples of the organic solvent include: organic solvents, such as alcohols (for example, ethanol), esters (for example, ethyl acetate), ketones (for example, acetone), and hydrocarbons (for example, hexane); fats (for example, medium-chain fatty acid triglycerides); and the like. The organic solvent is preferably an alcohol, a ketone, or a fat, specifically preferably ethanol, an acetone medium-chain fatty acid triglyceride, or the like. The organic solvents may be used singularly, or used in mixture of two or more kinds thereof. Alternatively, such an organic solvent may be used in the form of a hydrous solvent. However, to reduce the amount of the below-mentioned glycyrrhizic acid (glycyrrhizin) to a low level, the extraction solvent preferably has a lower hydrous ratio.

As the hydrophobic licorice extract, the extract extracted using an organic solvent may be used directly or may be used after being partially purified or well purified, for example, by column treatment, deodorization, decolorization, and/or the like in a further purifying step.

The amount of the polyphenol contained in the hydrophobic licorice extract is subject to no particular limitation, and is preferably 50 wt % or more, more preferably 60 wt % or more, still more preferably 70 wt % or more.

<Transthyretin Tetramer Stabilizing Agent>

A transthyretin tetramer stabilizing agent according to the present invention has the effect of stabilizing the transthyretin tetramer, and suppressing the monomerization of the transthyretin. Stabilizing the transthyretin tetramer makes it possible to suppress the transthyretin tetramer from being formed into amyloid. The present inventors have discovered that the polyphenol mixture has a markedly higher effect of stabilizing the transthyretin tetramer, compared with glabridin alone, which is conventionally known for achieving the effect of stabilizing the transthyretin tetramer.

The origin of a transthyretin as a subject for stabilization is subject to no particular limitation, and is usually a mammal, preferably a human. The amino acid sequence of a transthyretin may be a wild-type, or may have a mutation.

In one embodiment, the transthyretin tetramer stabilizing agent according to the present invention can be used in applications in which the agent in the form of a pharmaceutical product, food or drink product, or the like is administered to a subject or ingested by a subject, and stabilizes the transthyretin tetramer in vivo, for example, in the blood or the cerebrospinal fluid in the subject.

In addition, an embodiment of the present invention relates to a method of stabilizing a transthyretin tetramer in a subject, including:

administering a polyphenol mixture including glabridin, glabrene, and glabrol to a subject in need of the stabilization of the transthyretin tetramer; and suppressing, in the subject, the monomerization of the transthyretin tetramer and/or the formation of amyloid fibrils derived from the transthyretin tetramers.

A subject for the transthyretin tetramer stabilizing agent according to the present invention and the method of stabilizing the transthyretin tetramer according to the present invention is a human or a non-human animal in need of the stabilization of the transthyretin tetramer, preferably a human. Examples of the non-human animal include farm animals, pet animals, competition animals, and the like.

Examples of the farm animals include, but are not limited particularly to: domestic animals, such as horses, cattle, pigs, sheep, goats, camels, and llamas; laboratory animals, such as mice, rats, guinea pigs, and rabbits; and domestic fowls, such as chickens, ducks, turkeys, and ostriches. Examples of the pet animals include, but are not limited particularly to, dogs, cats, and the like. Examples of the competition animals include, but are not limited particularly to, race horses and the like. The non-human animal is particularly preferably a mammal.

The frequency of administration of, and the amount of administration of, the transthyretin tetramer stabilizing agent according to the embodiment to a subject can be suitably adjusted in accordance with the age, gender, condition, and the like of the subject. The amount of the transthyretin tetramer stabilizing agent to be administered per day can be adjusted suitably, and can be, for example, 0.01 to 100 mg/kg of body weight, preferably 0.1 to 30 mg/kg of body weight, as the daily total amount of the polyphenol. The frequency of administration per day can be adjusted suitably, and can be, for example, once or more, twice or more, or five times or less. The above-mentioned examples of the amount of administration and the frequency of administration are particularly preferable in cases where the subject is an adult. The route of administration may be oral administration or parenteral administration, and is preferably oral administration.

In another embodiment, the transthyretin tetramer stabilizing agent according to the present invention is present in an ex vivo sample containing the transthyretin tetramer, and can thus be used in applications in which the transthyretin tetramer is stabilized in the sample. Examples of the sample include blood containing the transthyretin tetramer, a sample derived from a body fluid, such as the cerebrospinal fluid, and a solution containing the transthyretin tetramer.

Yet another embodiment of the present invention relates to a method of stabilizing a transthyretin tetramer ex vivo, including:

bringing a polyphenol mixture including glabridin, glabrene, and glabrol in contact with the transthyretin tetramer present ex vivo; and suppressing the monomerization of the transthyretin tetramer and/or the formation of amyloid fibrils derived from the transthyretin tetramer.

The transthyretin tetramer stabilizing agent can be that which contains the polyphenol mixture, and may be a composition further containing one or more other components (for example, a composition or pharmaceutical for stabilizing the transthyretin tetramer). Preferable embodiments of the transthyretin tetramer stabilizing agent will be described below.

<A Preventing Agent or Progression Suppressing Agent for Transthyretin Amyloidosis>

A preventing agent or progression suppressing agent for transthyretin amyloidosis according to the present invention is administered to a subject in need of treatment, the prevention of, or the suppression of the progression of, transthyretin amyloidosis, and can stabilize the transthyretin tetramer, and treat, prevent, or suppress the progression of, the formation of an amyloid from the transthyretin through the effect of suppressing the monomerization of the transthyretin. The present inventors have discovered that, compared with glabridin alone, which is conventionally known for achieving the effect of stabilizing the transthyretin tetramer, the polyphenol mixture has a markedly higher effect of stabilizing the transthyretin tetramer, and accordingly has a markedly higher activity for treating, preventing, or suppressing the progression of, transthyretin amyloidosis.

In addition, another embodiment of the present invention relates to a method of treating, preventing, or suppressing the progression of, transthyretin amyloidosis in a subject, including:

administering a polyphenol mixture including glabridin, glabrene, and glabrol to a subject in need of the prevention of, or the suppression of progression of, transthyretin amyloidosis; and suppressing, in the subject, the monomerization of the transthyretin tetramer and/or the formation of an amyloid fibril from the transthyretin tetramer.

In an embodiment, a subject for a preventing agent or progression suppressing agent for transthyretin amyloidosis according to the present invention and for a method of treating, preventing, or suppressing the progression of, transthyretin amyloidosis according to the present invention is a human or a non-human animal in need of the treatment of, prevention of, or the suppression of the progression of, transthyretin amyloidosis, preferably human. Specific examples of the subject are as above-mentioned in relation to the transthyretin tetramer stabilizing agent.

The frequency of administration of, and the amount of administration of, a treating agent, preventing agent or progression suppressing agent for transthyretin amyloidosis according to the embodiment to a subject can be suitably adjusted in accordance with the age, gender, condition, and the like of the subject. The amount of the preventing agent or progression suppressing agent for transthyretin amyloidosis to be administered per day can be adjusted suitably, and can be, for example, 0.01 to 100 mg/kg of body weight, preferably 0.1 to 30 mg/kg of body weight, as the daily total amount of the polyphenol. The frequency of administration per day can be adjusted suitably, and can be, for example once or more and five times or less. The above-mentioned examples of the amount of administration and the frequency of administration are particularly preferable in cases where the subject is an adult. The route of administration may be oral administration or parenteral administration, and is preferably oral administration.

The treating agent, preventing agent or progression suppressing agent for transthyretin amyloidosis can be that which contains the polyphenol mixture, and may be a composition further containing one or more other components (for example, a composition or pharmaceutical for preventing, or suppressing the progression of, transthyretin amyloidosis). Preferable embodiments of the preventing agent or progression suppressing agent for transthyretin amyloidosis will be described below.

Examples of the transthyretin amyloidosis to be treated, prevented or suppressed from progression include senile systemic amyloidosis and familial amyloid polyneuropathy.
<Preferable Embodiments of Transthyretin Tetramer Stabilizing Agent and Preventing Agent or Progression Suppressing Agent for Transthyretin Amyloidosis>

Hereinafter, the transthyretin tetramer stabilizing agent and the treating agent, preventing agent or progression suppressing agent for transthyretin amyloidosis are collectively referred to as the "agent according to the present invention".

The agent according to the present invention can be that which contains the polyphenol mixture, may be that which is composed of the polyphenol mixture alone, or may be a composition containing the polyphenol mixture and one or more other components. The one or more other components can be, for example, one or more components acceptable as food products (ordinary food products, food products for specified health use, food products with function claims, dietary supplements, and the like), pharmaceutical products (pharmaceutical products for humans or pharmaceutical products for non-human animals), quasi-drugs, cosmetics, or animal feeding stuff (domestic animal feeding stuff or pet foods). Examples of the one or more other components acceptable as food products, pharmaceutical products, quasi-drugs, cosmetics, or animal feeding stuff include the below-described components that can be contained in the agent according to the present invention, and are other than the polyphenol mixture.

The total amount of the glabridin, glabrene, and glabrol or the total amount of the glabridin, glabrene, glabrol, and 4'-O-methylglabridin, contained in the agent according to the present invention, is subject to no particular limitation. The lower limit is preferably 0.1 wt % or more or 1 wt % or more, more preferably 4 wt % or more, 5 wt % or more, 9 wt % or more, or 10 wt % or more. The upper limit of the above-mentioned total amount in the agent according to the present invention is subject to no particular limitation. The more the amount, the more preferable. The amount is preferably 99 wt % or less, more preferably 90 wt % or less, taking account of containing another effective component(s) in a necessary amount.

The amount of the glabridin contained in the agent according to the present invention is subject to no particular limitation. The lower limit is preferably 0.1 wt % or more, 1 wt % or more, or 4 wt % or more. In addition, the upper limit is subject to no particular limitation, and is preferably 90 wt % or less, 85 wt % or less, 80 wt % or less, 70 wt % or less, or 60 wt % or less, taking account of mixing in another polyphenol or component.

In cases where the agent according to the present invention is ingested by a subject, or administered to the subject, it is preferable that the agent according to the present invention contains glabridin preferably in an amount of 0.40 to 4000 mg, more preferably in an amount of 4 mg to 1200 mg, per one ingestion or dosage unit. In cases where the agent according to the present invention is a food product, one ingestion or dosage unit refers to the amount of the food product to be ingested in at a time. For example, in cases where the amount of the food product to be ingested in at a time is packaged in a bottle or a can in fun-size form, or is packaged individually, one ingestion or dosage refers to one packaging unit. In cases where the agent according to the present invention is a pharmaceutical product, one ingestion or dosage unit refers to the recommended amount of the pharmaceutical product to be administered at a time.

In a preferable embodiment of the agent according to the present invention, the amount of glycyrrhizic acid (also referred to as glycyrrhizin) is preferably equal to or less than the amount of the polyphenol contained in the composition on a weight basis, and further preferably equal to or less than the amount of the glabridin. Depending on the extraction condition, the hydrophobic licorice extract can contain a component other than a polyphenol, and, for example, contain glycyrrhizic acid that is a hydrophilic component. For the agent according to the present invention which contains a hydrophobic licorice extract as a polyphenol mixture, the amount of the glycyrrhizic acid is preferably smaller from the viewpoint of safety in long-term ingestion or administration. The glycyrrhizic acid content of the agent according to the present invention is preferably substantially zero or small, for example, 0.005 wt % or less, preferably 0.001 wt % or less.

The agent according to the present invention may further contain a medium-chain fatty acid triglyceride. From the viewpoint of handling, the polyphenol mixture or the hydrophobic licorice extract containing the polyphenol mixture is preferably used in the form of a material dissolved in a medium-chain fatty acid triglyceride. In this case, the medium-chain fatty acid triglyceride to be used is subject to no particular limitation as long as the triglyceride is constituted by a $C_{6-12}$ fatty acid. The triglyceride as a main component is preferably constituted by a $C_{8-10}$ saturated fatty acid, more preferably constituted by a $C_8$ saturated fatty acid. The ratio of the constituent fatty acid in the medium-chain fatty acid triglyceride is subject to no particular limitation. The constituent ratio of the $C_{8-10}$ fatty acid is preferably 50 wt % or more, more preferably 70 wt % or more. In addition, a medium-chain fatty acid triglyceride having a specific gravity of 0.94 to 0.96 at 20° C. and a viscosity of 23 to 28 cP at 20° C. is particularly preferable. These medium-chain fatty acid triglycerides may be naturally-occurring, or may be prepared by transesterification or the like.

In addition, the medium-chain fatty acid triglyceride may be a glycerin fatty acid ester containing a medium-chain fatty acid triglyceride. The medium-chain fatty acid triglyceride is preferably a glycerin fatty acid ester containing a medium-chain fatty acid triglyceride in an amount of 50 wt % or more, more preferably a glycerin fatty acid ester containing a medium-chain fatty acid triglyceride in an amount of 70 wt % or more.

In addition, the agent according to the present invention may further contain a partial glyceride together with the medium-chain fatty acid triglyceride. It is also possible that, in place of the medium-chain fatty acid triglyceride, a partial glyceride of a medium-chain fatty acid is used. The partial glyceride is a glycerin fatty acid ester containing a partial glyceride, preferably a glycerin fatty acid ester containing a partial glyceride in an amount of 50 wt % or more, more preferably a glycerin fatty acid ester containing a partial glyceride in an amount of 70 wt % or more. Here, the partial glyceride is a diglyceride (1,2-diacylglycerol or 1,3-diacylglycerol) or a monoglyceride (1-monoacylglycerol or 2-monoacylglycerol). Any one of these may be used, or a mixture of two or more thereof may be used. A diglyceride is preferable from the viewpoint of processability. In addition, the partial glyceride may be naturally-occurring, or may be prepared by transesterification or the like. A fatty acid residue that constitutes the partial glyceride is, for example, a $C_{4-24}$ fatty acid residue, particularly preferably a $C_{8-10}$ medium-chain fatty acid residue. From among these, a saturated fatty acid, an unsaturated fatty acid, or the like can be selected depending on the application. For example, an unsaturated fatty acid is preferable in cases where fluidity is desired, and a saturated fatty acid is preferable in cases where plasticity is desired. In addition, a branched fatty acid such as an isostearic acid can be used.

The agent according to the present invention can contain another component to be used for preparation, besides the polyphenol mixture. Examples of the another component to be used for preparation include an excipient, a disintegrator, a lubricant, a binder, an antioxidant, a colorant, an aggregation inhibitor, an absorption enhancer, a solubilizer for an effective component, a stabilizer, a fat, a viscosity modifier, and the like.

Examples of the excipient include, but are not limited particularly to, saccharose, lactose, dextrose, corn starch, mannitol, crystalline cellulose, calcium phosphate, calcium sulfate, magnesium sulfate, and the like.

Examples of the disintegrator include, but are not limited particularly to, starch, agar, calcium citrate, calcium carbonate, sodium hydrogencarbonate, dextrin, crystalline cellulose, carboxy methyl cellulose, tragacanth, and the like.

Examples of the lubricant include, but are not limited particularly to, talc, magnesium stearate, polyethylene glycol, silica, hydrogenated vegetable oil, and the like.

Examples of the binder include, but are not limited particularly to, ethyl cellulose, methyl cellulose, hydroxypropylmethyl cellulose, tragacanth, shellac, gelatin, gum arabic, polyvinylpyrrolidone, polyvinyl alcohol, polyacrylic acid, polymethacrylic acid, sorbitol, and the like.

Examples of the antioxidant include, but are not limited particularly to, ascorbic acid, tocopherol, sodium bisulfate, sodium thiosulfate, sodium pyrosulfite, citric acid, and the like.

Examples of the colorant include, but are not limited particularly to, a colorant permitted to be added to pharmaceutical products, food products, or the like.

Examples of the aggregation inhibitor include, but are not limited particularly to, stearic acid, talc, light anhydrous silicic acid, hydrated silicate dioxide, and the like.

Examples of the absorbefacient include, but are not limited particularly to, higher alcohols; higher fatty acids; sucrose fatty acid esters; surfactants, such as a sorbitan fatty acid ester, a polyoxyethylene sorbitan fatty acid ester, and a polyglycerin fatty acid ester; and the like.

Examples of the solubilizer for an effective component include, but are not limited particularly to, organic acids, such as fumaric acid, succinic acid, malic acid, and the like.

Examples of the stabilizer include, but are not limited particularly to, benzoic acid, sodium benzoate, ethyl paraoxybenzoate, propylene glycol, and the like.

Examples of the fat component that can be used include, but are not limited particularly to: vegetable oils, such as corn oil, rapeseed oil, high erucic rapeseed oil, soybean oil, olive oil, safflower oil, cottonseed oil, sunflower oil, rice-bran oil, beefsteak plant oil, perilla oil, linseed oil, evening primrose oil, cacao butter, peanut oil, palm oil, and palm kernel oil; animal oils, such as fish oil, beef tallow, lard, milk fat, and egg yolk oil; fats obtained by separation, hydrogenation, transesterification, or the like using any of these as a raw material; and oil mixtures thereof.

Examples of the viscosity modifier include, but are not limited particularly to, beeswax, Japan tallow, lanolin, microcrystalline wax, liquid paraffin, and the like.

The agent according to the present invention may be, for example, in the form of a food product (an ordinary food product, a food product for specified health use, a food product with function claims, a dietary supplement, or the like), a pharmaceutical product (a pharmaceutical product for humans or a pharmaceutical product for non-human animals), a quasi-drug, a cosmetic, or animal feeding stuff (domestic animal feeding stuff or a pet food), preferably in the form of a food product or a pharmaceutical product.

In cases where the agent according to the present invention is in the form of a food product, a pharmaceutical product, a quasi-drug, animal feeding stuff, or livestock feed, the agent may be in the form of a preparation for oral ingestion. Examples of the preparation for oral ingestion include one in orally ingestible form, such as a tablet, a capsule (a hard capsule, a microcapsule, and a soft capsule), a granule, a powder, a chewable preparation, a syrup, and a liquid. Examples of a capsule base material for the agent to be formed into a capsule include, but are not limited particularly to: gelatins derived from cattle bone, cattle skin, pig skin, fish skin, or the like can to be used. Moreover, examples of other base materials usable as food additives may include: those derived from seaweed, for example, carageenan and alginic acid; those derived from plants or seeds, for example, Locust bean gum and guar gum; those derived from microorganism, for example, pullulan and curdlan; and manufacturing agents which contain celluloses can to be also used.

In addition, the agent according to the present invention may be in the form of a common food product. Examples of the common food product include, but are not limited to: drinks, such as lactic drinks, soft drinks, nutrient drinks, and drinks for beauty; confectionery, such as chewing gums, chocolates, candies, jellies, cakes, biscuits, and crackers; frozen desserts, such as ice creams and ices; noodles, such as udon noodles, Chinese noodles, spaghetti, and instant noodles; paste products, such as boiled fish pastes, chikuwa pastes, and hanpen pastes; seasonings, such as dressings, mayonnaises, and sauces; bread; hams; rice gruel; cooked rice; soups; various kinds of retort pouch food products; various kinds of frozen food products; and the like.

In cases where the agent according to the present invention is in the form that is other than a pharmaceutical product, and is a food product that can be ingested for the maintenance of health, such as a food product for specified health use, a food product with function claims, or a dietary supplement, the agent according to the present invention may be contained in a package, and the package may be labelled as having a function related to stabilizing the transthyretin tetramer and preventing, or suppressing the progression of, transthyretin amyloidosis. Examples of the package include, but are not limit particularly to, boxes, containers, package films, wrapping paper, and the like. In addition, the function labelled on the package may be expressed in a different manner, as long as the function is similar to those above-mentioned.

Furthermore, the agent according to the present invention may be in the form of a parenteral agent. For example, the agent can be in the form of an agent that is applied directly to the skin. In this case, examples of the dosage form include, but are not limited particularly to: an agent (ointment, liniment, lotion, spray agent, or the like) obtained by dissolving or mixing/dispersing the above-mentioned component(s) in a suitable base, and forming the resulting product into a cream, a paste, a jelly, a gel, a milky liquid, or a liquid: an agent (cataplasm or the like) obtained by dissolving or mixing/dispersing the above-mentioned composition(s) in a base, and spreading the resulting product on a support; an agent (plaster, tape, or the like) obtained by dissolving or mixing/dispersing the above-mentioned composition(s) in an adhesive, and spreading the resulting product on a support.

In cases where the agent according to the present invention is in the form of a quasi-drug, the quasi-drug refers to a quasi-drug provided in "Act on Securing Quality, Efficacy and Safety of Products Including Pharmaceuticals and Medical Devices". Examples of the quasi-drug include oral agents (liquid agents, such as extract agents, elixir agents, syrup agents, tincture agents, and lemonade agents; and solid agents, such as capsules, granules, pills, powders, and tablets) and the like.

EXAMPLES

Example 1

<Sample Preparation>

An ethanol solution in an amount of 63.9 g containing 135 mg of glabrene, 921 mg of glabridin, 184 mg of glabrol, and 160 mg of 4'-O-methylglabridin and 18.8 g of a medium-chain fatty acid triglyceride (Actor M2, manufactured by Riken Vitamin Co., Ltd., with the fatty acid composition of C8:C10=99:1) were mixed, and the resulting mixture was allowed to be concentrated under vacuum, whereby the ethanol was removed. From 28.7 g of the material obtained by the vacuum concentration, the insoluble components were collected by suction filtration, and then, the insoluble components were washed with hexane. The resulting oil collected was added to the previous filtrate. To 26.2 g of the filtrate collected, 4.5 g of a medium-chain fatty acid triglyceride was added to obtain 30.7 g of a medium-chain fatty acid triglyceride solution containing a polyphenol mixture (containing 1.4 g of the polyphenol mixture).

In this regard, the amount of the polyphenol contained in the medium-chain fatty acid triglyceride solution was measured by a polyphenol analysis based on a Folin-Denis method using glabridin (a commercially available reagent) as a standard substance. In addition, the amount of the glycyrrhizic acid was determined to be 0.005 wt % or less by the following analysis method.

(HPLC Conditions for Glycyrrhizic Acid Analysis)
Column: YMC J'sphere ODS-H80, 4.6 mm in inner diameter×250 mm in length (YMC Co., Ltd.)
Column temperature: 40° C.
Mobile phase A: acetonitrile
Mobile phase B: 20 mM phosphoric acid water solution
Gradient: the ratio of the mobile phase A to the total amount of the mobile phase A and the mobile phase B was constant at 36% after the start of analysis until 10 minutes after the start, then increased to 45% at a constant ratio after the 10 minutes until 50 minutes, then constant at 100% after the 50 minutes until 55 minutes, and constant at 36% after the 55 minutes until 75 minutes.
Flow rate: 1 mL/min
Wavelength: UV 254 nm
Amount of sample injected: 20 μL <Analysis of Peak Intensity of Each Polyphenol>
In methanol for HPLC, 1 g of the medium-chain fatty acid triglyceride solution containing the polyphenol mixture was dissolved, and the total amount was adjusted to 100 mL.

(HPLC Conditions for Polyphenol Analysis)
Column: YMC J'sphere ODS-H80, 4.6 mm in inner diameter×250 mm in length (YMC Co., Ltd.)
Column temperature: 40° C.
Mobile phase A: acetonitrile:methanol (1:1=v/v)
Mobile phase B: 20 mM phosphoric acid water solution
Gradient: the ratio of the mobile phase A to the total amount of the mobile phase A and the mobile phase B was constant at 50% (v/v) after the start of analysis until 20 minutes after the start, then increased to 80% (v/v) at a constant ratio after the 20 minutes until 75 minutes, then constant at 100% (v/v) after the 75 minutes until 80 minutes, and constant at 50% (v/v) after the 80 minutes until 100 minutes.
Flow rate: 1.0 mL/min
Wavelength: UV 282 nm
Amount of sample injected: 20 μL <Analysis Results>

In an HPLC analysis under the above-mentioned conditions in which the sample was a medium-chain fatty acid triglyceride solution containing a polyphenol mixture, the peak intensity of the glabrene was 38%, the peak intensity of the glabrol was 44%, and the peak intensity of the 4'-O-methylglabridin was 19%, in cases where the peak intensity (peak area) of the glabridin was regarded as 100%.

The amount of each component contained in 1 g of the medium-chain fatty acid triglyceride solution containing the polyphenol mixture was as follows: glabrene (4.4 mg), glabridin (30.0 mg), glabrol (6.0 mg), and 4'-O-methylglabridin (5.2 mg). The amount of each component was measured using a calibration curve prepared from the result of an HPLC analysis of a commercially available standard substance containing a known concentration of the component.

<Polyphenol Content Analysis>

The polyphenol content was measured by a Folin-Denis method using glabridin (a commercially available reagent) as a standard substance, with the result that the total amount of polyphenol contained in 1 g of the medium-chain fatty acid triglyceride solution containing the polyphenol mixture was 239.1 mg.

Example 2

<Sample Preparation>

Ethanol solutions 1 to 4 containing a polyphenol mixture were prepared in such a manner that the respective peak intensities (peak areas) of glabrene, glabrol, and 4'-O-methylglabridin to the glabridin in an HPLC analysis under the above-mentioned conditions are the values in the following Table. The solution in an amount of 64.0 g and 19.0 g of the medium-chain fatty acid triglyceride were mixed, and the resulting mixture was allowed to be concentrated under vacuum, whereby the ethanol was removed. Then, 4.5 g of a medium-chain fatty acid triglyceride was added to the liquid obtained by vacuum concentration, whereby a medium-chain fatty acid triglyceride solution containing a polyphenol mixture was obtained.

TABLE 1

| Peak Intensity (%, to Glabridin) | Solution 1 | Solution 2 | Solution 3 | Solution 4 |
|---|---|---|---|---|
| Glabridin | 100 | 100 | 100 | 100 |
| Glabrene | 41 | 41 | 40 | 39 |
| Glabrol | 44 | 45 | 45 | 46 |
| 4'-O-Methylglabridin | 17 | 19 | 19 | 19 |

Example 3

<Stabilization Test 1 of Transthyretin Tetramer>

Serums were obtained from blood taken from three middle-aged and older persons. The medium-chain fatty acid triglyceride solution containing a polyphenol mixture and the glabridin that were obtained in Example 1 were added to each serum (added in such a manner that the amount of the glabridin was 0, 10, and 50 μM respectively). The resulting mixtures were incubated at 25° C. for 30 minutes, and then denatured with urea. Using these samples, the transthyretins (the tetramers, the dimers, and the monomers) in the serum were quantitated by electrophoresis and Western blotting. The stabilization effect was investigated using the ratio of the monomers (monomer) to the total amounts of the transthyretins (total) (monomer/total) and the ratio of the tetramers (tetramer) to the total amounts of the transthyretins (total) (tetramer/total). The analysis results of the monomer/total ratio are shown in the left of FIG. 1. The analysis results of the tetramer/total ratio are shown in the right of FIG. 1.

With the glabridin alone added at the concentrations up to 50 μM, the ratio of the monomers to the total amounts of the transthyretins did not change, and the ratio of the tetramers to the total amounts of the transthyretins did not increase, as shown in FIG. 1. The stabilization effect for the transthyretin was not observed. On the other hand, in the cases where the medium-chain fatty acid triglyceride solution containing the polyphenol mixture was added at the largest concentration, the effect (the stabilization of transthyretin) was observed in which the ratio of the monomers to the total amounts of the transthyretins was decreased, and the ratio of the tetramers to the total amounts of the transthyretins was increased.

Example 4

<Stabilization Test 2 of Transthyretin Tetramer>

Over a period of 4 weeks, three healthy persons took in that medium-chain fatty acid triglyceride solution containing the polyphenol mixture which was obtained in Example 1 (the amount of ingestion, 600 mg/day). Blood was collected at time intervals, whereby plasma was obtained. The plasma of each person was incubated at 25° C. for 30 minutes, and then, denatured with urea. Using these samples, the transthyretins (the tetramers and the monomers) in the plasma were quantitated by electrophoresis and Western blotting. The stabilization effect was investigated using the ratio of the monomers to the tetramers (monomer/tetramer). The results are shown in FIG. 2.

Figure 2:
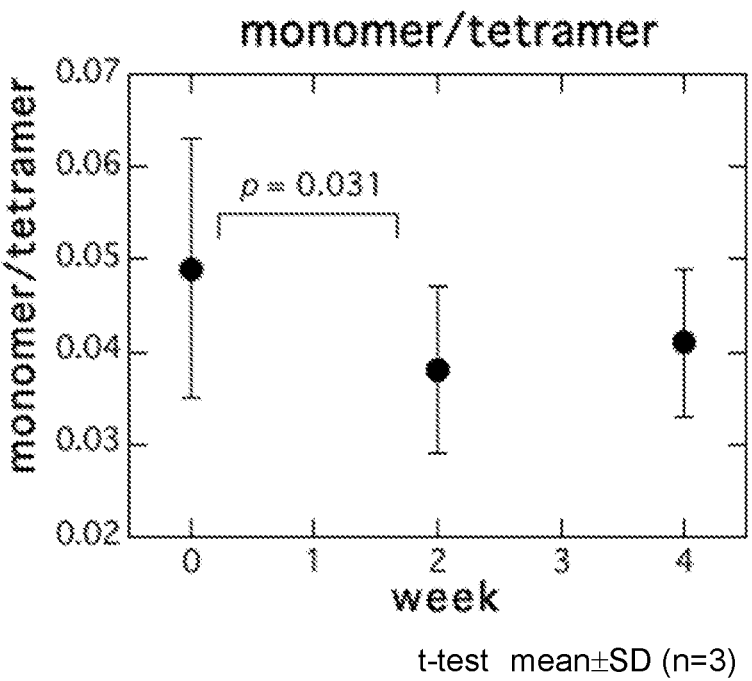
FIG. 2 shows the ratios of the transthyretin monomers to the tetramers (monomer/tetramer) in plasma in Example 4, in which a medium-chain fatty acid triglyceride solution containing a polyphenol mixture had been ingested to humans over a period of 4 weeks (the amount of ingestion was 600 mg/day), from whom the plasma was obtained at time intervals. A lower ratio demonstrates that the stability of the transthyretin tetramer is higher.

As shown in FIG. 2, the ratio between the monomers and the tetramers was decreased after 2 weeks of supplementation with the medium-chain fatty acid triglyceride solution containing the polyphenol mixture. Specifically, the effect of decreasing the ratio of the monomers and increasing the tetramers (the stabilization of transthyretin) was found.

As above-mentioned, the polyphenol mixture can stabilize the transthyretin tetramer, decrease the ratio of the monomers contained in vivo, and increase the tetramer.

All the publications, patents, and patent applications cited herein are incorporated herein by reference in their entireties.

The invention claimed is:

1. A transthyretin tetramer stabilizing agent comprising glabridin, glabrene, glabrol, and 4'-O-methylglabridin, wherein the transthyretin tetramer stabilizing agent exhibits any one or more of the characteristics b), c), and d) under the following conditions a) in an HPLC analysis:

a) mobile phase: acetonitrile:methanol=1:1 (mobile phase A) and 20 mM phosphoric acid (mobile phase B) in gradient elution; column: ODS column; flow rate: 1.0 mL/minute; temperature: 40° C.; detector: UV detector; and wavelength of detection: 282 nm;

b) a ratio of a glabrene peak intensity to a glabridin peak intensity is 38% or more and 41% or less;

c) a ratio of a glabrol peak intensity to a glabridin peak intensity is 44% or more and 47% or less; and d) a ratio of a 4'-O-methylglabridin intensity to a glabridin peak intensity is 15% or more and 20% or less.

2. The transthyretin tetramer stabilizing agent according to claim 1, wherein the content of glycyrrhizic acid is 0.005 wt % or less.

3. A treating agent or progression suppressing agent for transthyretin amyloidosis comprising glabridin, glabrene, glabrol, and 4'-O-methylglabridin, wherein the treating agent or progression suppressing agent for transthyretin amyloidosis exhibits one or more of the characteristics b), c), and d) under the following conditions a) in an HPLC analysis:

a) mobile phase: acetonitrile:methanol=1:1 (mobile phase A) and 20 mM phosphoric acid (mobile phase B) in gradient elution; column: ODS column; flow rate: 1.0 mL/minute; temperature: 40° C.; detector: UV detector; and wavelength of detection: 282 nm;

b) a ratio of a glabrene peak intensity to a glabridin peak intensity is 38% or more and 41% or less;

c) a ratio of a glabrol peak intensity to a glabridin peak intensity is 44% or more and 47% or less; and d) a ratio of a 4'-O-methylglabridin intensity to a glabridin peak intensity is 15% or more and 20% or less.

4. The treating agent or progression suppressing agent for transthyretin amyloidosis according to claim 3, wherein the transthyretin amyloidosis is senile systemic amyloidosis or familial amyloid polyneuropathy.

5. The transthyretin tetramer stabilizing agent according to claim 1, in the form of a tablet, a capsule, a granule, or a powder.

6. The transthyretin tetramer stabilizing agent according to claim 1, comprising the glabridin in an amount of 4 mg to 1200 mg per one ingestion or dosage unit.

7. A method of treating, or suppressing the progression of, transthyretin amyloidosis in a subject in need thereof, comprising:

administering an effective amount of a polyphenol mixture including glabridin, glabrene, and glabrol to a subject in need of the suppression of progression of, transthyretin amyloidosis; and suppressing, in the subject, the monomerization of a transthyretin tetramer and/or the formation of amyloid fibrils from the transthyretin tetramer.

8. The method according to claim 7, wherein the polyphenol mixture is administered in an amount of 0.01 to 100 mg/kg of body weight per day.

9. A pharmaceutical composition comprising the transthyretin tetramer stabilizing agent according to claim 1, or the treating agent or progression suppressing agent for transthyretin amyloidosis according to claim 3.

10. The pharmaceutical composition according to claim 9 in the form of a tablet, a capsule, a granule, or a powder.

11. The pharmaceutical composition according to claim 9 comprising glabridin in an amount of 4 mg to 1200 mg per dosage.

12. A method of treating senile systemic amyloidosis or familial amyloid polyneuropathy comprising administering an effective amount of a polyphenol mixture comprising glabridin, glabrene, and glabrol to a subject in need of such treatment.

13. The method according to claim 12, wherein the polyphenol mixture is administered in an amount of 0.01 to 100 mg/kg of body weight per day.

14. A method of stabilizing a transthyretin tetramer in a subject in need thereof, comprising:

administering an effective amount of a polyphenol mixture including glabridin, glabrene, glabrol, and 4'-O-methylglabridin to a subject in need of the stabilization of a transthyretin tetramer; and suppressing, in the subject, the monomerization of a transthyretin tetramer and/or the formation of amyloid fibrils from the transthyretin tetramer.

15. The method according to claim 14, wherein the polyphenol mixture is administered in an amount of 0.01 to 100 mg/kg of body weight per day.

* * * * *